United States Patent [19]

Sawaki et al.

[11] Patent Number: 6,093,835
[45] Date of Patent: *Jul. 25, 2000

[54] PROCESS FOR PRODUCING MALEIC ANHYDRIDE

[75] Inventors: Itaru Sawaki; Hideo Suwa; Yasunori Ishimura; Tatsuya Ihara, all of Okayama, Japan

[73] Assignee: Mitsubishi Chemical Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/119,723

[22] Filed: Jul. 21, 1998

[30] Foreign Application Priority Data

Jul. 22, 1997 [JP] Japan ................................. 9-195549

[51] Int. Cl.⁷ .................................................. C07D 307/34
[52] U.S. Cl. ........................... 549/259; 549/256; 549/258; 549/262
[58] Field of Search ..................... 549/259, 256, 549/258

[56] References Cited

U.S. PATENT DOCUMENTS

| | | | |
|---|---|---|---|
| 4,118,403 | 10/1978 | White | 549/262 |
| 4,472,527 | 9/1984 | Otake et al. | 502/209 |
| 4,520,127 | 5/1985 | Otake et al. | 502/209 |
| 5,631,387 | 5/1997 | Brown et al. | 549/262 |

FOREIGN PATENT DOCUMENTS

| | | |
|---|---|---|
| 0 459 543 | 12/1991 | European Pat. Off. . |
| 49-29168 | 8/1974 | Japan . |
| 59-205373 | 11/1984 | Japan . |
| 60-143832 | 7/1985 | Japan . |
| 1-25747 | 5/1989 | Japan . |
| 1-503211 | 11/1989 | Japan . |
| 4-24104 | 4/1992 | Japan . |
| 8-9606 | 1/1996 | Japan . |
| 8-245610 | 9/1996 | Japan . |
| 96/29323 | 9/1996 | WIPO . |

OTHER PUBLICATIONS

Gabriele Centi, et al., "Mechanistic Aspects of Maleic Anhydride Synthesis from $C_4$ Hydrocarbons over Phosphorus Vanadium Oxide," Chem. Rev. 1988, 88, pp. 55–80.

European Search Report issued on Mar. 4, 1999, in corresponding PCT Application No. 98 11 3683.

Primary Examiner—Bernard Dentz
Attorney, Agent, or Firm—Oblon, Spivak, McClelland, Maier & Neustadt, P.C.

[57] ABSTRACT

A process for producing maleic anhydride is described, which comprises (i) reacting a hydrocarbon with oxygen in a vapor phase in the presence of a catalyst to yield a reaction mixture gas containing maleic anhydride, (ii) bringing the reaction mixture gas into contact with an organic solvent to collect the maleic anhydride in the organic solvent, (iii) separating at least part of the maleic anhydride from the organic solvent, (iv) washing with an aqueous alkali solution at least part of the organic solvent from which maleic anhydride has been separated, and (v) reusing the resultant washed organic solvent and the residual organic solvent for contact with the reaction mixture gas.

8 Claims, 3 Drawing Sheets

PROCESS FOR MALEIC ANHYDRIDE RECOVERY WITH ORGANIC SOLVENT

PROCESS FOR MALEIC ANHYDRIDE RECOVERY IN WHICH ORGANIC SOLVENT IS WASHED WITH ALKALI SOLUTION

PROCESS IN WHICH ORGANIC SOLVENT IS WASHED WITH ALKALI SOLUTION AND THEN WITH WATER

PROCESS FOR PRODUCING MALEIC ANHYDRIDE

FIELD OF THE INVENTION

The present invention relates to a process for producing maleic anhydride. More particularly, this invention relates to an improvement in a process for producing maleic anhydride in which a reaction mixture gas containing maleic anhydride produced by catalytically oxidizing a hydrocarbon in a vapor phase is brought into contact with an organic solvent to thereby collect the maleic anhydride contained in the gas with the organic solvent.

BACKGROUND OF THE INVENTION

The production of maleic anhydride through the catalytic oxidation of a hydrocarbon in a vapor phase is well known. Although benzene and air have conventionally been used as starting materials for the oxidation reaction in the presence of a vanadium pentoxide catalyst in the above process, techniques have recently been developed in which a chain hydrocarbon having 4 carbon atoms, e.g., butane, butene, or butadiene, is used as a starting material. The mainstream technique among these is to use n-butane, which is a saturated hydrocarbon, as a starting material and conduct the oxidation reaction thereof in the presence of a catalyst comprising a vanadium-phosphorus mixed oxide as the active component.

The maleic anhydride contained in the yielded reaction mixture gas is recovered, for example, by cooling the reaction mixture gas to condense the maleic anhydride, or by bringing the reaction mixture gas into contact with water to collect the maleic anhydride as maleic acid in the water. However, these recovery techniques each has problems inherent therein.

The technique for recovering maleic anhydride which is currently thought to be the most preferred is to bring a reaction mixture gas into contact with an organic solvent to collect maleic anhydride in the organic solvent. For example, in U.S. Pat. No. 4,118,403 is disclosed a technique in which a reaction mixture gas is contacted in an absorption column with a dialkyl phthalate in which each alkyl group has 2 to 8 carbon atoms to thereby collect maleic anhydride. The dialkyl phthalate containing maleic anhydride absorbed therein is stripped or distilled to recover the maleic anhydride therefrom, and the residual dialkyl phthalate is cooled and then circulated to the absorption tower. In JP-B-1-25747 (the term "JP-B" as used herein means an "examined Japanese patent publication") is disclosed the use of a dialkyl ester of a hydrogenated phthalic acid, such as tetrahydrophthalic acid or hexahydrophthalic acid, in place of a dialkyl phthalate.

One of the problems of the techniques in which an organic solvent is circulated to recover maleic anhydride is that by-products of the reaction such as acrylic acid, maleic acid, fumaric acid, and high-boiling components are collected in the organic solvent and accumulate in the apparatus to plug or soil the apparatus. In the case where a phthalic ester or the like is used as the organic solvent, phthalic acid or the like is yielded by solvent decomposition and arouses the same problem. These accumulated components further accelerate decomposition of the solvent and, as a result, pose a problem that the solvent consumption per unit production of maleic anhydride increases and the production cost of maleic anhydride increases. Expedients which have been proposed for eliminating these problems include a technique in which filtration and distillation are conducted (see U.S. Pat. No. 4,118,403) and a technique of washing a circulating organic solvent with water (see European Patent 0459543). However, even with these techniques, the problems caused by the accumulation of impurities in an organic solvent are difficult to mitigate to a satisfactory level.

It is known that in the case of using a catalyst comprising a vanadium-phosphorus mixed oxide as the active component, an effective method for maintaining the catalytic activity is to feed a phosphorus compound to the reactor (see, for example, JP-A-59-205373 and JP-A-60-143832 (the term "JP-A" as used herein means an "unexamined published Japanese patent application")). It is thought that since phosphorus as one of the constituent elements of the catalyst vaporizes off during the reaction, the addition of a phosphorus compound in such a manner as to compensate for the vaporization loss can maintain the catalytic performance at a constant level. Consequently, when the reaction mixture gas, which contains phosphorus compounds resulting from vaporization from the catalyst, is contacted with an organic solvent, these phosphorus compounds also are collected in the organic solvent together with maleic anhydride. As a result of investigations made by the inventors of the present invention, it has been found that an organic solvent containing these phosphorus compounds is more susceptible to decomposition than the same organic solvent not containing these phosphorus compounds, and that these phosphorus compounds are difficult to remove by mere washing with water.

SUMMARY OF THE INVENTION

An object of the present invention is to provide an efficient process for producing maleic anhydride which is free from the problems attributable to impurity accumulation in an organic solvent used for recovering maleic anhydride from a reaction mixture gas. More particularly, the object of the present invention is to provide a means for eliminating the problems that the accumulation of specific impurities in an organic solvent causes plugging of the apparatus and that the impurity accumulation accelerates decomposition of the solvent to increase the solvent consumption.

The inventors of the present invention made intensive studies in order to eliminate the problems described above. As a result, they have found that when an organic solvent containing impurities including phosphorus compounds or the like is washed with an aqueous alkali solution, the impurities can be easily removed, whereby the organic solvent can be inhibited from decomposition and maleic anhydride can be produced efficiently. The present invention has been completed based on this finding.

The present invention provides (1) a process for producing maleic anhydride which comprises (i) reacting a hydrocarbon with oxygen in a vapor phase in the presence of a catalyst to yield a reaction mixture gas containing maleic anhydride, (ii) bringing the reaction mixture gas into contact with an organic solvent to collect the maleic anhydride in the organic solvent, (iii) separating at least part of the maleic anhydride from the organic solvent, (iv) washing with an aqueous alkali solution at least part of the organic solvent from which maleic anhydride has been separated, and (v) reusing the resultant washed organic solvent and the residual organic solvent for contact with the reaction mixture gas.

According to preferred embodiments of the present invention, the following are provided: (2) the process described above wherein the reaction of a hydrocarbon with oxygen is conducted in the presence of a phosphorus-vanadium mixed oxide catalyst; (3) the process described above wherein the hydrocarbon is a chain hydrocarbon having 4 carbon atoms; (4) the process described above wherein the aqueous alkali solution has an alkali concentration of 0.005N or higher; (5) the process described above wherein the aqueous alkali solution is an aqueous sodium hydroxide solution or an aqueous ammonia solution; (6) the process described above wherein the washing is conducted at 30 to 90° C.; (7) the process described above wherein the organic solvent is a dialkyl ester of either phthalic acid or a hydrogenated phthalic acid; and (8) the process described above wherein the organic solvent from which maleic anhydride was at least partly separated and which thereafter was washed at least partly with an aqueous alkali solution is further washed with water or waste washing water in one or more stages, before the washed organic solvent and the residual organic solvent are reused for contact with the reaction mixture gas.

DETAILED DESCRIPTION OF THE INVENTION

Figure 1:
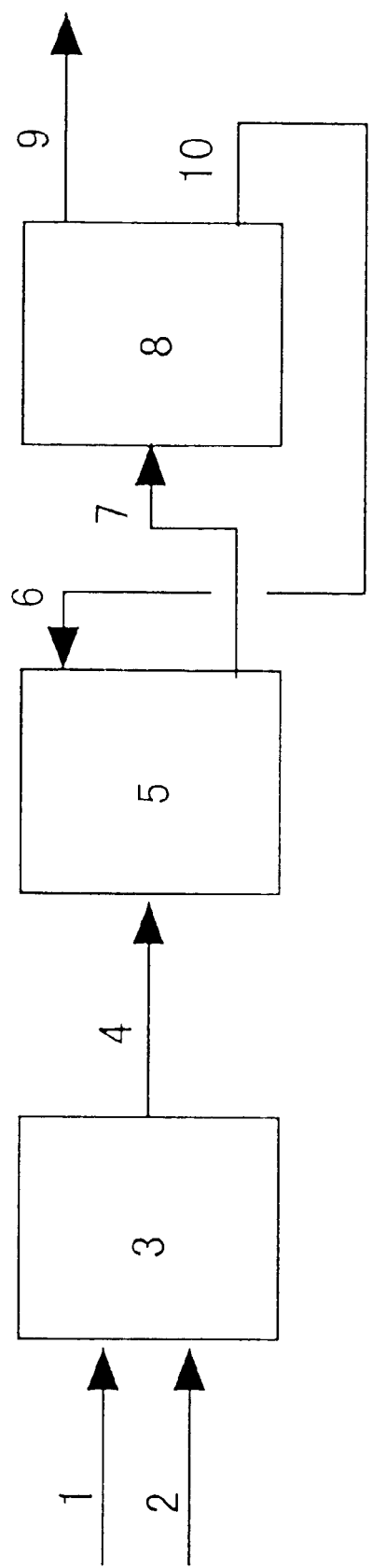
FIG. 1 is a flow diagram illustrating a process for maleic anhydride recovery with an organic solvent.

In the process of the present invention, a hydrocarbon is reacted with oxygen in a vapor phase in the presence of a catalyst to yield a reaction mixture gas containing maleic anhydride, and this reaction mixture gas is brought into contact with an organic solvent to collect the maleic anhydride in the organic solvent, from which the maleic anhydride is recovered.

The catalyst used here is one comprising as the active component a mixed oxide containing vanadium and phosphorus as major constituent elements (vanadium-phosphorus mixed oxide). Especially preferred among this kind of catalysts are those comprising divanadyl pyrophosphate $((VO)_2P_2O_7)$ as the active component, which are known to exhibit excellent performances. These catalysts themselves are known and used ordinarily. Details of these catalysts including production processes are disclosed, for example, in *Chem. Rev.*, 88, pp. 55–80 (1988), JP-B-4-24104, and U.S. Pat. Nos. 4,472,527 and 4,520,127.

Examples of the feedstock hydrocarbon generally include chain hydrocarbons having 4 carbon atoms, such as butane (n-butane), butenes (1-butene and 2-butene), and butadiene (1,3-butadiene). Preferred among these is butane.

As the oxygen gas is generally used air. However, air diluted with an inert gas, air enriched with oxygen, or the like may also be used.

The reaction is carried out in a fluidized-bed reactor or a fixed-bed reactor. A feedstock hydrocarbon and an oxygen-containing gas, usually air, are fed to the reactor in such a proportion as to result in a feedstock hydrocarbon concentration of about from 1.5 to 10%, and are reacted at 300 to 600° C. Methods for this reaction in a fluidized-bed or fixed-bed reactor themselves are known and used ordinarily. Details thereof are given, for example, in JP-B-49-29168, JP-B-8-9606, JP-W-1-503211 (the term "JP-W" as used herein means an "unexamined published international patent application"), JP-A-8-245610, and *Kirk-Othmer Encyclopedia of Chemical Technology*, 4th ed., Vol. 15, pp. 905–914, John Wiley & Sons, Inc.

The reaction mixture gas discharged from the reactor contains the oxygen and feedstock hydrocarbon remaining unreacted, by-products such as carbon monoxide, carbon dioxide, and water, and other reaction products, besides maleic anhydride as the target reaction product.

The reaction mixture gas thus yielded is brought into contact with an organic solvent to collect the maleic anhydride in the organic solvent, from which the maleic anhydride is recovered.

Any organic solvent may be used for collecting maleic anhydride from the reaction mixture gas without particular limitations as long as it is capable of dissolving maleic anhydride therein, has a high boiling point, and is insoluble in the aqueous alkali solution to be used. In general, a dialkyl ester of either phthalic acid or a hydrogenated phthalic acid in which each alkyl group has 1 to 4 carbon atoms is used. Examples thereof include the dimethyl, diethyl, dipropyl, diisopropyl, dibutyl, or diisobutyl esters of phthalic acid, dihydrophthalic acid, tetrahydrophthalic acid, and hexahydrophthalic acid. Preferred among these is dibutyl phthalate. Also usable are dimethylbenzophenone, dichlorodiphenyl oxide, and the like.

For collecting maleic anhydride with an organic solvent and recovering the maleic anhydride from the organic solvent, an ordinary method which itself is known may be used without particular limitations. An example thereof will be schematically explained below by reference to FIG. 1.

A feedstock hydrocarbon (1) and an oxygen-containing gas (2) are introduced into a reactor (3) containing a catalyst comprising a vanadium-phosphorus mixed oxide as the active component. The gas (4) yielded by the reaction is introduced into an absorption column (5) for maleic anhydride absorption, into which an organic solvent (6) is also introduced. The organic solvent (7) containing maleic anhydride absorbed therein is introduced into a separation column (8) for separating the maleic anhydride from the organic solvent. In the separation column, the maleic anhydride is separated from the organic solvent based on a difference in boiling point therebetween. From the separation column are discharged crude maleic anhydride (9) as the target reaction product and the residual organic solvent (10) from which most of the maleic anhydride has been separated. The residual organic solvent from which most of the maleic anhydride has been removed is returned to the absorption column (5) and thus circulated and used.

In the process of the present invention, at least part of the organic solvent from which maleic anhydride has been at least partly separated is washed with an aqueous alkali solution and then the resultant washed organic solvent and the residual organic solvent are reused for contact with the reaction mixture gas.

The aqueous alkali solution used for washing the organic solvent may be an aqueous solution of any of various known alkalis such as, e.g., sodium hydroxide, potassium hydroxide, sodium carbonate, sodium hydrogen carbonate, potassium carbonate, potassium hydrogen carbonate, and ammonia. Among these, however, an aqueous sodium hydroxide solution or an aqueous ammonia solution is preferably used. The concentration of the aqueous alkali solution is generally 0.005N or higher, preferably 0.01N or higher. If the aqueous alkali solution has too low a concentration, a reduced washing efficiency may result. Furthermore, since too high a concentration may result in side-reactions, the upper limit of the alkali concentration is preferably 5N, more preferably 3N. Namely, the concentration of the aqueous alkali solution is in the range of preferably from 0.005 to 5N, more preferably from 0.01 to 3N.

For washing the organic solvent with an aqueous alkali solution, any of various known apparatuses may be used, such as a stirring vessel and a line mixer. Although a stationary vessel may be used for separating the aqueous alkali solution from the organic solvent, it is preferred to use a centrifugal separator, a coalescer, or the like. The proportion of the organic solvent to the aqueous alkali solution varies depending on-the apparatus used. However, the amount of the organic solvent per part by weight of the aqueous alkali solution is generally from 1 to 10 parts by weight, preferably from 2 to 6 parts by weight. The washing is conducted preferably at 30 to 90° C., more preferably at 40 to 70° C.

In general, an alkali component tends to remain in a slight amount in the organic solvent which has undergone washing with an aqueous alkali solution. When this organic solvent containing a slight amount of an alkali component is circulated for reuse and heated in the absorption column or the separation column, the alkali component undergoes chemical reactions with the organic solvent and with the acid contained therein. These reactions give undesirable results such as accelerated decomposition of the organic solvent, impurity inclusion into maleic anhydride, and the like. It is therefore preferred to add a washing step for removing the alkali component present in a slight amount from the organic solvent which has undergone washing with an aqueous alkali solution.

The washing of the organic solvent which has undergone alkali washing is desirably conducted to such a degree that the amount of the alkali component (e.g., the amount of sodium or nitrogen when sodium hydroxide or ammonia, respectively, was used for alkali washing) remaining in the washed organic solvent is generally 10 ppm or smaller, preferably 5 ppm or smaller, more preferably 1 ppm or smaller by weight.

The washing step for removing an alkali component from the organic solvent which has undergone alkali washing may be conducted in one or more stages according to the efficiency of alkali component removal. Water is preferably used as a washing liquid. However, in the case where the washing is conducted in multiple stages, it is possible to employ such a constitution that water is used only as the washing liquid for the final stage, the waste washing water discharged from the final stage is used as the washing water for the stage just before the final stage, and the waste washing water discharged therefrom is used as the washing water for the stage just before that stage, in order to reduce the use amount of water.

This washing step for removing an alkali component from the organic solvent which has undergone alkali washing can be carried out in the same manner as the step of washing with an aqueous alkali solution. Namely, this washing step can be accomplished by mixing the organic solvent with a washing water by means of any of various ordinary mixing apparatuses, e.g., a stirring vessel or a line mixer, and then separating the solvent from the water with a stationary vessel, centrifugal separator, coalescer, or the like. The proportion of the organic solvent to the washing water (water or wastewater) is such that the amount of the organic solvent per part by weight of the washing water is generally from 1 to 10 parts by weight, preferably from 2 to 6 parts by weight. This washing is conducted at a temperature of preferably from 30 to 90° C., more preferably from 40 to 70° C.

As described above, in the process of the present invention, the production of maleic anhydride by the catalytic oxidation of a hydrocarbon, the collection of the maleic anhydride contained in the reaction mixture gas with an organic solvent, and the separation of the maleic anhydride from the organic solvent can be conducted according to ordinary methods. Although the washing of the organic solvent with an aqueous alkali solution may be conducted with respect to all the organic solvent to be circulated, it is generally preferred to wash part of the organic solvent. This is because the organic solvent to be circulated usually contains maleic anhydride remaining unrecovered and the washing of this organic solvent with an aqueous alkali solution results in the loss of the maleic anhydride. It is therefore preferred that the organic solvent to be circulated be distilled to recover the maleic anhydride contained therein, and then part of the organic solvent be taken out and subjected to washing with an aqueous alkali solution.

Figure 2:
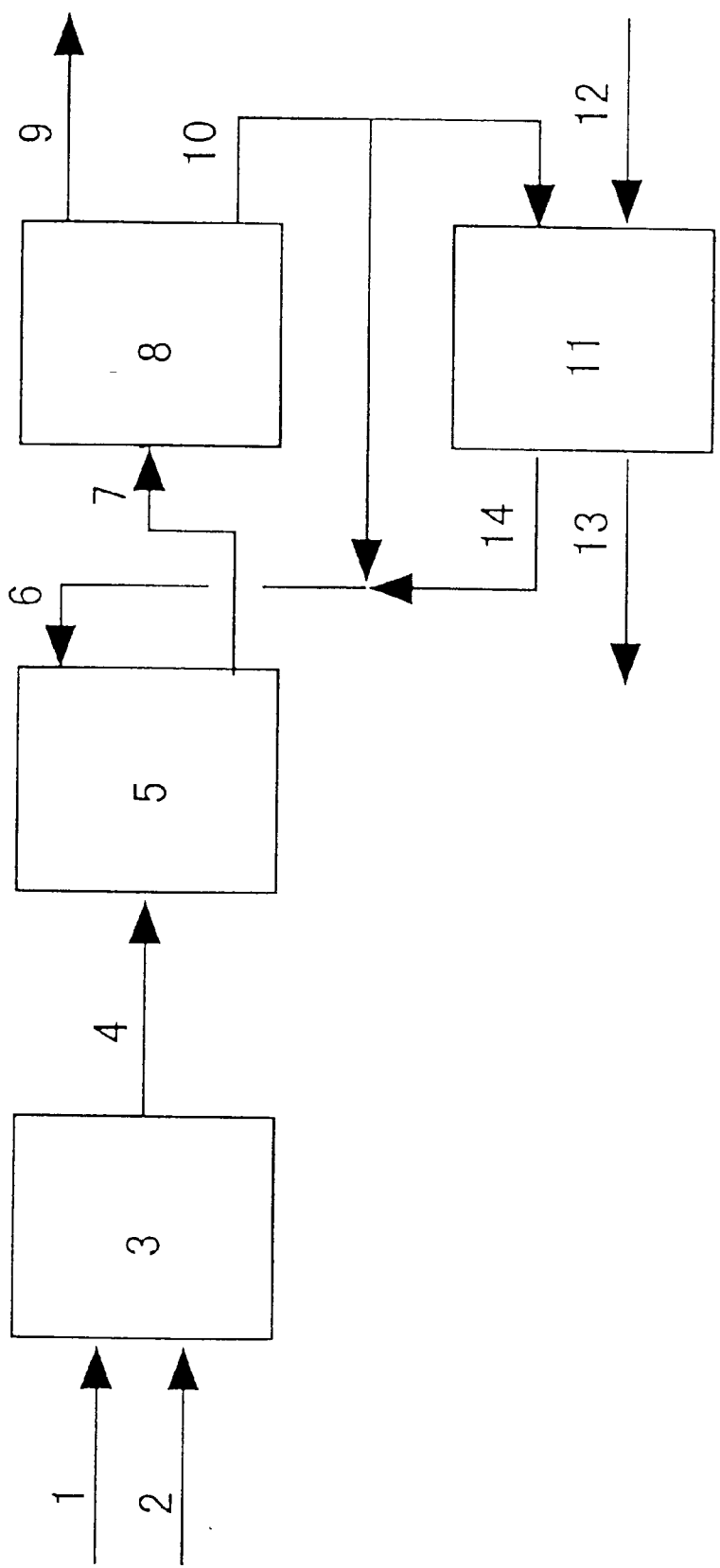
FIG. 2 is a flow diagram illustrating a process for maleic anhydride recovery in which the organic solvent is washed with an aqueous alkali solution.

One embodiment of the present invention is schematically shown in FIG. 2. The whole constitution of this process is substantially the same as that of the process shown in FIG. 1, except the following. The residual organic solvent (10) from which most-of the maleic anhydride was removed in the separation column (8) is discharged. Part or all of the organic solvent (10) is introduced into a solvent washing equipment (11), and is contacted therein with an aqueous alkali solution (12). Impurities (13) contained in the organic solvent are discharged, while the organic solvent (14) from which the impurities have been removed by the washing and the residual organic solvent, if any, is returned to the absorption column (5) and is thus circulated and reused.

Figure 3:
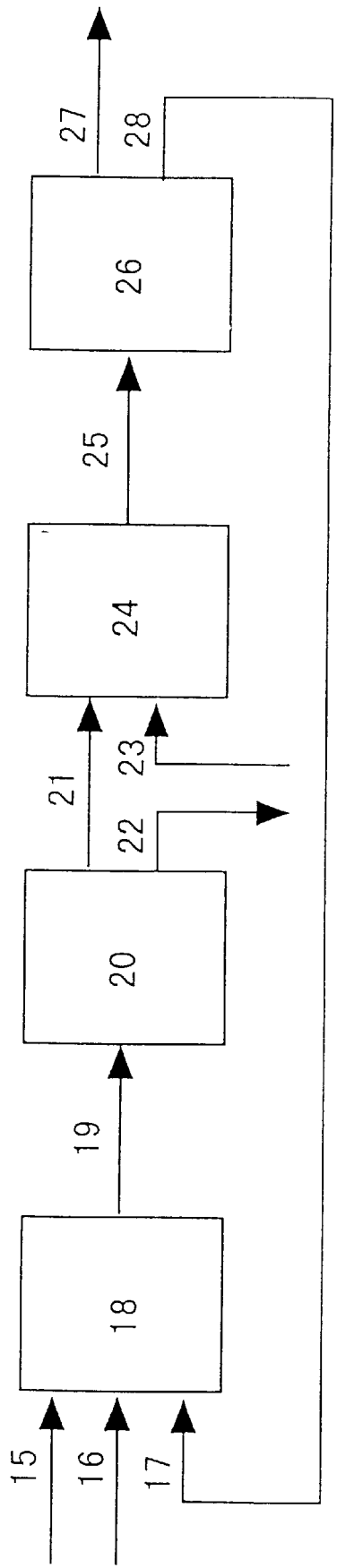
FIG. 3 is a flow diagram illustrating a process in which the organic solvent is washed with an aqueous alkali solution and then with water.

FIG. 3 is a schematic illustration showing one embodiment of the process in which the organic solvent washed with an aqueous alkali solution is further washed in multiple stages while effectively utilizing waste washing water. The organic solvent to be washed (15), an aqueous alkali solution (16), and a waste washing water (17) resulting from second washing are introduced into a first mixing vessel (18), where the organic solvent is sufficiently mixed with the aqueous alkali solution. The resultant mixed liquid (19) is introduced into a first oil/water separator (20), where the mixed liquid (19) is separated into an organic solvent layer and an aqueous layer. The organic solvent (21) is introduced into a second mixing vessel (24), while the wastewater (22) is discharged. Water (23) is introduced into the second mixing vessel and mixed with the organic solvent (21) in order to remove the alkali component remaining in a slight amount in the organic solvent (21). The resultant mixed liquid (25) is introduced into a second oil/water separator (26), where the mixed liquid (25) is separated again into an organic solvent layer and an aqueous layer. The resultant washed organic solvent (27) and the residual organic solvent, if any, is returned to the absorption column and is thus circulated and reused, while the wastewater (28) is returned to the first mixing vessel (18) and used. The above are mere examples for illustrating embodiments of the present invention and the invention should never be construed as being limited thereto.

The present invention will be explained below in more detail by reference to Examples, but the invention should not be construed as being limited thereto.

EXAMPLES 1 TO 12 AND COMPARATIVE EXAMPLES 1 TO 5

Orthophosphoric acid was added to dibutyl phthalate in an amount of 50 ppm in terms of phosphorus amount. This mixture was heated at 220° C. for 23 hours in a nitrogen atmosphere. Upon analysis, it was found that tributyl phosphate, dibutyl phosphate, and monobutyl phosphate had generated in amounts of 13 ppm, 14 ppm, and 20 ppm, respectively, in terms of phosphorus amount, and that phthalic anhydride as a solvent decomposition product had formed in an amount of 0.15%. To this solution were added maleic anhydride, fumaric acid, and phthalic anhydride in such amounts as to result in concentrations of 189 ppm, 302 ppm, and 1.02%, respectively.

Two hundred grams of this solvent was mixed with 50 g of each of washing liquids respectively having the compositions shown in Table 1. Each mixture was stirred under the conditions shown in Table 1, and then allowed to stand for 30 minutes to cause oil/water separation. The results obtained are shown in Table 2.

TABLE 1

Washing Conditions

| | Washing water | Alkali concentration (N) | Washing water/ solvent (weight ratio) | Stirring period (min) | Temperature (°C.) |
|---|---|---|---|---|---|
| Example 1 | aq. NaOH solution | 0.0625 | 0.25 | 30 | 40 |
| Example 2 | aq. NaOH solution | 0.125 | 0.25 | 30 | 40 |
| Example 3 | aq. NaOH solution | 0.25 | 0.25 | 30 | 40 |
| Example 4 | aq. NaOH solution | 0.5 | 0.25 | 30 | 40 |
| Example 5 | aq. NaOH solution | 1 | 0.25 | 30 | 40 |
| Example 6 | aq. NaOH solution | 1.5 | 0.25 | 30 | 40 |
| Example 7 | aq. NaOH solution | 2 | 0.25 | 30 | 40 |
| Example 8 | aq. NaOH solution | 0.25 | 0.25 | 30 | 80 |
| Example 9 | aq. NaOH solution | 1 | 0.25 | 30 | 80 |
| Example 10 | aq. NH$_3$ solution | 0.41 | 0.25 | 30 | 40 |
| Example 11 | aq. NH$_3$ solution | 0.82 | 0.25 | 30 | 40 |
| Example 12 | aq. NH$_3$ solution | 1.6 | 0.25 | 30 | 40 |
| Comparative Example 1 | pure water | — | 0.25 | 30 | 40 |
| Comparative Example 2 | pure water | — | 0.25 | 5 | 40 |
| Comparative Example 3 | pure water | — | 0.25 | 10 | 40 |
| Comparative Example 4 | pure water | — | 0.25 | 10 | 60 |
| Comparative Example 5 | pure water | — | 0.25 | 10 | 80 |

TABLE 2

Percentage of Removal of Each Component by Washing (%)

| | Water-soluble phosphorus[1] | Phthalic anhydride[2] | Fumaric acid[3] | Maleic anhydride[4] |
|---|---|---|---|---|
| Example 1 | 33.3 | 23.2 | 77.2 | 100.0 |
| Example 2 | 72.2 | 30.0 | 81.5 | 100.0 |
| Example 3 | 90.6 | 41.7 | 100.0 | 100.0 |
| Example 4 | 100.0 | 74.5 | 92.7 | 100.0 |
| Example 5 | 95.0 | 100.0 | 100.0 | 100.0 |
| Example 6 | 96.7 | 100.0 | 100.0 | 100.0 |
| Example 7 | 94.4 | 100.0 | 100.0 | 100.0 |
| Example 8 | 76.1 | 95.1 | 89.7 | 100.0 |
| Example 9 | 97.8 | 100.0 | 100.0 | 100.0 |
| Example 10 | 92.2 | 38.1 | 91.1 | 98.4 |
| Example 11 | 95.0 | 74.6 | 92.1 | 97.9 |
| Example 12 | 100.0 | 91.2 | 87.1 | 96.3 |
| Comparative Example 1 | 22.2 | 14.3 | 80.1 | 100.0 |
| Comparative Example 2 | 27.8 | 23.2 | 85.4 | 88.0 |
| Comparative Example 3 | 22.2 | 10.2 | 80.7 | 96.9 |
| Comparative Example 4 | 16.7 | 9.4 | 77.7 | 100.0 |
| Comparative Example 5 | 11.1 | 22.9 | 80.7 | 100.0 |

(1) Percentage of removal of water-soluble phosphorus:
   [(phosphorus concentration before washing)–(phosphorus concentration after washing)]/[(phosphorus concentration washing)]×100
(2) Percentage of removal of phthalic anhydride:
   {(phthalic anhydride concentration before washing)–[(phthalic anhydride concentration after washing)+(phthalic acid concentration after washing)]}/(phthalic anhydride concentration before washing)×100
(3) Percentage of removal of maleic anhydride:
   {(maleic anhydride concentration before washing)–[(maleic anhydride concentration after washing)+(maleic acid concentration after washing)]}/(maleic anhydride concentration before washing)×100
(4) Percentage of removal of fumaric acid:
   [(fumaric acid concentration before washing)–(fumaric acid concentration after washing)]/(fumaric acid concentration before washing)×100

EXAMPLE 13

Two hundred grams of a solvent prepared under the same conditions as in Example 1 was mixed with 50 g of 0.59N aqueous ammonia solution. This mixture was stirred at 40° C. for 30 minutes and then allowed to stand for 10 minutes. The solvent was thereafter taken out. Because this solvent had undergone insufficient oil/water separation, it contained nitrogen in an amount of 30 ppm. To this solvent was added 50 g of water. The resultant mixture was stirred at 40° C. for 30 minutes and then allowed to stand for 30 minutes, before the solvent was taken out. This solvent contained nitrogen in an amount of 0.6 ppm.

EXAMPLE 14

An experiment for actually recovering maleic anhydride with a test apparatus having the constitution shown in FIG. 2 was conducted using dibutyl phthalate as a solvent to examine the effect of the washing of the organic solvent with an aqueous alkali solution.

According to the method described in the Example 2 of JP-B-4-24104, a fluidized-bed catalyst comprising a vanadium-phosphorus mixed oxide as the active component was obtained. A fluidized-bed reactor having a diameter of 0.8 m was charged with 1,500 kg of this catalyst. n-Butane and air were used as feedstocks and reacted in the reactor at 430° C., at which the n-butane concentration in all the gases fed to the reactor was 4.2 vol %.

Part of the reaction mixture gas was introduced into the apparatus for maleic anhydride recovery whose constitution is shown in FIG. 2, and maleic anhydride was collected using dibutyl phthalate as a solvent. During this operation, the reactor effluent gas (4) was introduced into the absorption column (5) at a rate of about 100 Nm$^3$/hr, while the organic solvent (6) sent from the separation column (8) and the solvent washing equipment (11) was introduced into the absorption column (5) at a rate of 90 kg/hr. The solvent (7) discharged from the bottom of the absorption column had a maleic anhydride concentration of 7.7 wt %. This solvent was sent to the separation column (8), and was distilled therein at a pressure of 3.5 kPa and a bottom temperature of 215° C. to separate the acid from the solvent. Thus, crude maleic anhydride (9) and the organic solvent (10) were continuously discharged at rates of about 7.5 kg/hr and about 90 kg/hr, respectively. A 20 kg/hr portion of the solvent (10) discharged from the separation column was sent to the stirring/mixing vessel as the solvent washing equipment (11), and was continuously mixed therein with 0.35N aqueous ammonia solution (12) introduced at a rate of 5 kg/hr, under the conditions of 40° C. and an average residence time of 30 minutes. The resultant mixed liquid was sent to a stationary vessel and allowed to stand for 30 minutes to thereby separate the mixture into an organic solvent layer and an aqueous layer. Only the organic solvent (14) was returned to the absorption column and circulated for reuse, while the aqueous layer was treated as a wastewater (13). The liquid level of each of the columns, stirring vessel, and stationary vessel was controlled so as to keep the whole organic-solvent amount within the apparatus constant. In case of a solvent deficiency, the apparatus was suitably replenished with fresh organic solvent.

After the apparatus was continuously run for 3 days, the solvent discharged from the bottom of the separation column (8) had the following impurity concentrations.

| Phthalic anhydride | 0.14 wt % |
|---|---|
| Fumaric acid | 400 ppm |
| Total phosphorus | 4 ppm |

The amount of the organic solvent used for replenishment during the three days was 37 g/hr on the average, except for that which vaporized and entrained off from the top of the absorption column.

COMPARATIVE EXAMPLE 6

The same apparatus as in Example 14 was continuously run for 3 days under the same conditions as in Example 14, except that water was used in place of the aqueous ammonia solution for washing the organic solvent.

The solvent discharged from the bottom of the separation column (8) after the 3-day operation had the following impurity concentrations.

| Phthalic anhydride | 1.37 wt % |
|---|---|
| Fumaric acid | 500 ppm |
| Total phosphorus | 28 ppm |

The amount of the organic solvent used for replenishment during the three days was 225 g/hr on the average, except for that which vaporized and entrained off from the top of the absorption column.

A comparison between Example 14 and Comparative Example 6 clearly shows that the washing of an organic solvent with an aqueous alkali solution according to the present invention was effective in significantly lowering the concentrations of impurities accumulated in the solvent, in particular the concentrations of phthalic anhydride and phosphorus. It is also apparent that the organic solvent loss caused by decomposition was significantly inhibited.

In the process comprising catalytically oxidizing a hydrocarbon in a vapor phase in the presence of a catalyst to yield a reaction mixture gas containing maleic anhydride and then bringing the gas into contact with an organic solvent to recover the maleic anhydride, the washing of the organic solvent with an aqueous alkali solution according to the present invention is effective in diminishing the accumulation of impurities in the organic solvent and hence in eliminating the problems, for example, that the accumulation of impurities causes plugging of the apparatus and accelerates decomposition of the organic solvent. As a result, low-cost stable plant operation (efficient production of maleic anhydride) is possible over a prolonged period of time.

While the invention has been described in detail and with reference to specific embodiments thereof, it will be apparent to one skilled in the art that various changes and modifications can be made therein without departing from the spirit and scope thereof.

What is claimed is:

1. A process for producing maleic anhydride which comprises (i) reacting a hydrocarbon with oxygen in a vapor phase in the presence of a catalyst to yield a reaction mixture gas containing maleic anhydride, (ii) bringing the reaction mixture gas into contact with an organic solvent to collect the maleic anhydride in the organic solvent, (iii) separating at least part of the maleic anhydride from the organic solvent, (iv) washing with an aqueous alkali solution at least part of the organic solvent from which maleic anhydride has been separated, and (v) reusing the resultant washed organic solvent and the residual organic solvent for contact with the reaction mixture gas.

2. The process as claimed in claim 1, wherein the reaction of a hydrocarbon with oxygen is conducted in the presence of a phosphorus-vanadium mixed oxide catalyst.

3. The process as claimed in claim 1, wherein the hydrocarbon is a chain hydrocarbon having 4 carbon atoms.

4. The process as claimed in claim 1, wherein the aqueous alkali solution has an alkali concentration of 0.005 N or higher.

5. The process as claimed in claim 1, wherein the aqueous alkali solution is an aqueous sodium hydroxide solution or an aqueous ammonia solution.

6. The process as claimed in claim 1, wherein the washing is conducted at 30 to 90° C.

7. The process as claimed in claim 1, wherein the organic solvent is a dialkyl ester of either phthalic acid or a hydrogenated phthalic acid.

8. The process as claimed in claim 1, wherein the organic solvent from which maleic anhydride was at least partly separated and which thereafter was washed at least partly with an aqueous alkali solution is further washed with water or waste washing water in one or more stages, before the washed organic solvent and the residual organic solvent are reused for contact with the reaction mixture gas.

* * * * *